United States Patent [19]

Schwenke et al.

[11] 4,426,717
[45] Jan. 17, 1984

[54] MEASURING APPARATUS FOR X-RAY FLUORESCENCE ANALYSIS

[75] Inventors: Joachim Schwenke, Escheburg; Joachim Knoth, Hamburg; Rainer Marten; Herbert Rosomm, both of Geesthacht, all of Fed. Rep. of Germany

[73] Assignee: Gesellschaft für Kernenergieverwertung in Schiffbau und Schiffahrt mbH, Geesthacht-Tesperhude, Fed. Rep. of Germany

[21] Appl. No.: 133,556

[22] Filed: Mar. 24, 1980

Related U.S. Application Data

[63] Continuation of Ser. No. 933,883, Aug. 15, 1978, abandoned.

[30] Foreign Application Priority Data

Aug. 17, 1977 [DE] Fed. Rep. of Germany ....... 2736960

[51] Int. Cl.³ .......................................... G01N 23/22
[52] U.S. Cl. ..................................... 378/45; 378/70; 378/145
[58] Field of Search ...................... 378/45, 46, 48, 49, 378/70

[56] References Cited

U.S. PATENT DOCUMENTS 3,944,822  3/1976  Dyubay ................................ 378/45

Primary Examiner—Craig E. Church
Attorney, Agent, or Firm—Becker & Becker, Inc.

[57] ABSTRACT

A measuring apparatus for X-ray fluorescence analysis in which the specimen is stimulated by glancing incident radiation and is examined spectrometrically by a detector disposed above the specimen. In the path of rays of the stimulating X-radiation there is disposed a reflector which in operation deflects the X-radiation to the surface of the specimen.

3 Claims, 4 Drawing Figures

MEASURING APPARATUS FOR X-RAY FLUORESCENCE ANALYSIS

This is a continuation of application Ser. No. 933,833—Schwenke et al. filed Aug. 15, 1978, now abandoned.

The invention relates to measuring apparatus for X-ray fluorescence analysis, wherein the specimen is stimulated by glancing indicent radiation and is examined spectrometrically with a detector disposed over the specimen.

According to an earlier proposal by the Applicant (German Patent No. P 26 32 001.4), the stimulation of the specimen is effected by direct irradiation with X-rays, the specimen support being disposed on a pivoted frame which affords the possibility of altering the angle of the incident radiation to the specimen.

As further developments by the applicant have shown, the measuring apparatus described previously has certain disadvantages. A particular disadvantage lies in the fact that the highly energetic component of the spectrum of the stimulating radiation can only be influenced by altering the anode voltage of the X-ray tube. In this case, the X-ray tube generally has to be operated in a voltage range which is unfavorable for the radiation yield. The fact must also be taken into consideration that the highly energetic component of the stimulating radiation, which is fundamentally unwanted and which can no longer be reflected by the specimen support, has an unfavorable influence on the background. It may be mentioned as a further disadvantage that the angular adjustment of the specimen support involves relatively great technical expense.

It is therefore the object of the present invention to provide improved measuring apparatus for X-ray fluorescence analysis of the kind referred to hereinbefore, in which the highly energetic component of the stimulating radiation is substantially prevented from reaching the specimen support, the X-ray tube producing the stimulating radiation can be operated in a voltage range which is more favorable for the radiation yield, and the adjustment of the path of rays is simplified very considerably.

According to the invention, the above-mentioned problem is solved in that a reflector, which deflects the radiation to the surface of the specimen support, is disposed in the path of rays of the stimulating X-radiation.

As a result of the provision of a reflector, the highly energetic component of the stimulating radiation is cut off as by a low-pass filter. The position of the specimen support can now remain unaltered because the adjustment of the angle at which the stimulating radiation falls on the specimen support can now be effected by altering the position of the reflector plate and/or the position of the X-ray tube producing the stimulating radiation. Also, the adjustment is no longer so critical, particularly when, in accordance with further preferred features of the invention, the reflector is disposed surrounding the detector in the vicinity of the specimen support, preferably above the specimen support.

Further details and features of the invention are apparent from the following detailed description and the accompanying drawings in which a measuring apparatus according to the invention is illustrated diagrammatically.

Figure 1:
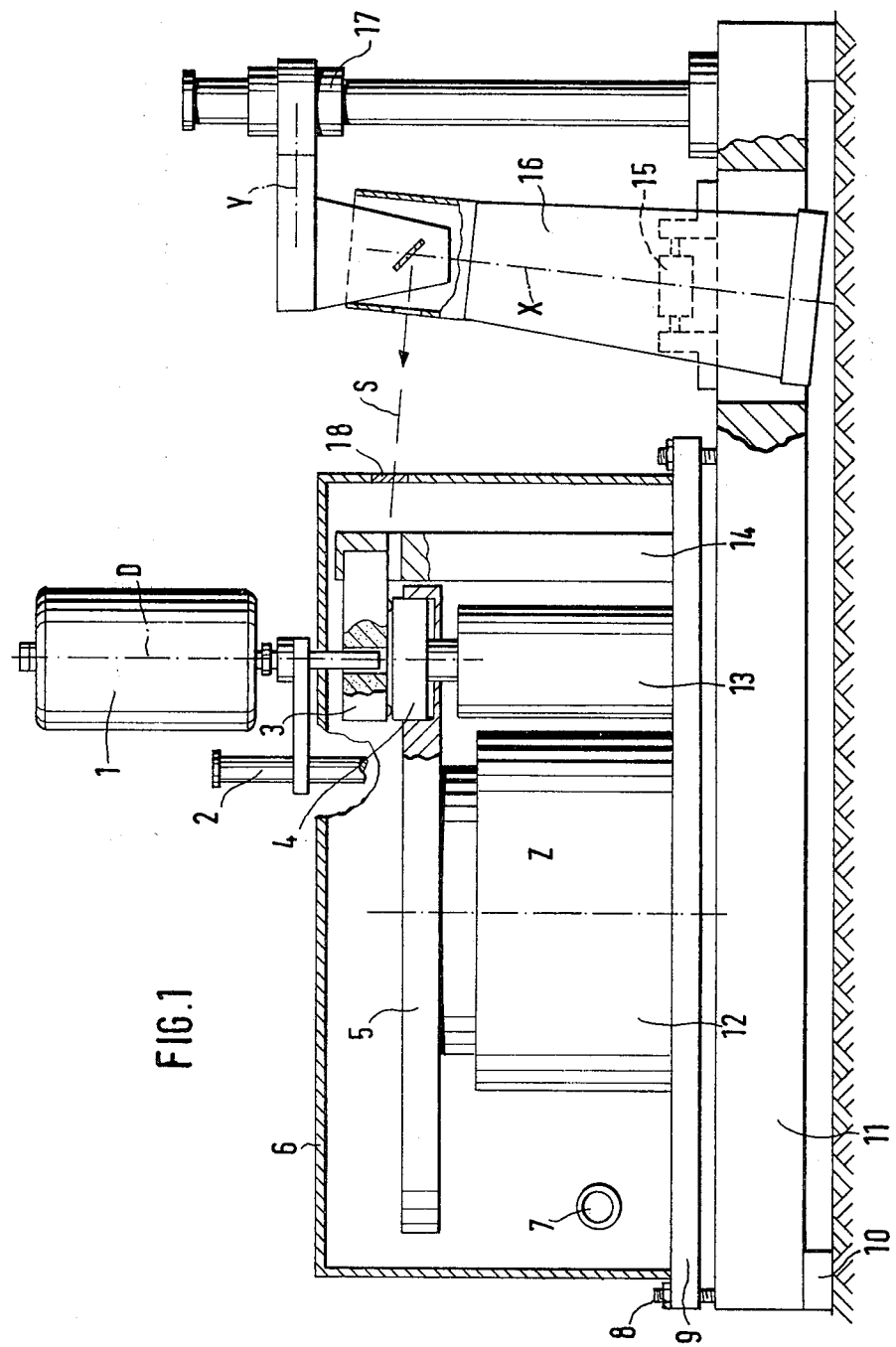
FIG. 1 shows a diagrammatic longitudinal section through a measuring apparatus according to the invention.

The detector system of the measuring apparatus shown in FIG. 1 consists in a known manner of a Dewar vessel with a detector 1, for example a Sili detector, a counter tube or an NaJ crystal, in an adjustable holding means 2 which also serves to aligh the detector axis D. The detector 1 is inserted through a seal in the hood 6 of a dust proof or vacuum housing provided with a charging flap. The hood 6, which may also receive a charge of protective gas (helium or the like) is sealingly supported at its lower edge on a base plate 9. The connection 7 provided in the hood 6 serves to produce the vacuum or for charging with a protective gas. The base plate 9 is mounted on a base 11 with adjusting screws 8 to adjust the measuring plane, and the base may likewise be provided with feet 10 which are adjustable in height, as indicated.

At the side of the hood 6, there is an entrace window 18 of beryllium. An external X-ray source 16, which may be an X-ray tube or a secondary target for example, can be placed in front of this window 18. The beryllium window 18 ensures that the stimulating X-radiation is weakened as little as possible. The X-ray source 16 is provided in the base 11, with an adjusting device 15 which affords the possibility of deflecting the vertical axis X of the X-ray tube. A further adjusting device 17 on a stand affords the possibility of aligning the X-ray tube 16 in height and with respect to the horizontal axis Y.

Inside the hood 6, on the base plate 9, is a positioning device 12 for the magazine 5 containing the specimen supports 4 (only one shown). The positioning device 12 or the specimen changer comprises a plate which is rotatable about the axis Z like a turn-table and which can receive the specimen magazine 5. This positioning device can be turned by means of a drive operated from the outside so that the specimen supports 4 contained in the specimen magazine 5 can be aligned in succession on the detector axis D. As the drawing shows, the individual specimen supports 4 lie with slight clearance in recesses in the specimen magazine 5. Beside the positioning device 12 is a pressure device 13 which, like the positioning device 12, can be moved by a drive operated from the outside. On activation of the pressure device 13, a ram presses from below through the turn-table plate and then moves the specimen support 4 into the measuring position.

Figure 3:
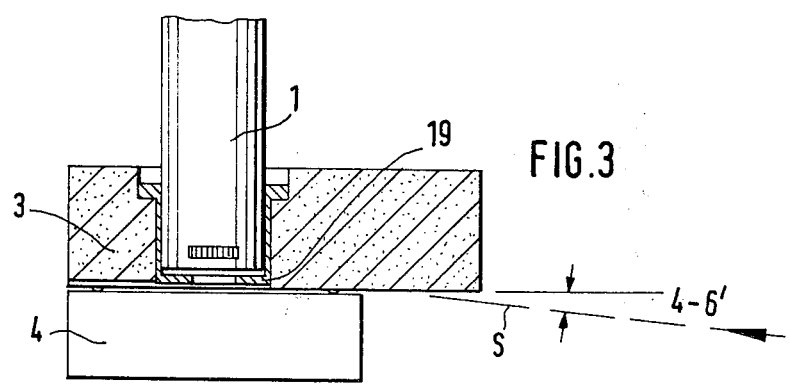
FIG. 3 shows an enlarged detail from FIG. 1.
Figure 4:
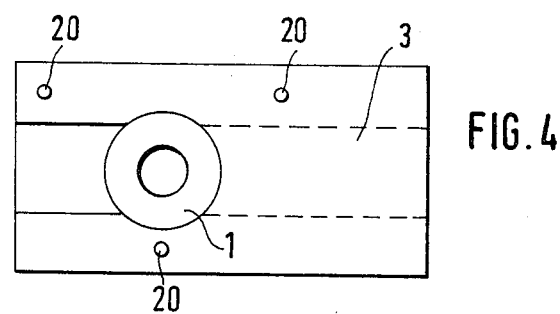
FIG. 4 shows a view of FIG. 3 from below.

Beside the pressure device 13 there is a bearing block 14 which extends vertically upwards and which carries, at its upper end, the reflector plate 3 provided according to the invention. This reflector plate 3 is drilled through, as FIGS. 3 and 4 show. The bore in the reflector plate 3 receives the front end of the detector 1. The detector 1 is mounted in the reflector plate 3 so that the aperture diaphragm 19 of the detector is aligned substantially coplanar with the front face of the reflector. At the underside of the reflector plate 3 there are three small knub-like abutments 20 against which the specimen support 4 can come to bear when it is raised into the working position by the pressure device.

When work is to be carried out with the measuring apparatus according to the invention, the X-ray tube 16 is switched on and then passes a beam of X-rays S through the beryllium window 18. Through an appropriate bore in the bearing block 14, this X-ray beam S reaches the underside of the reflector plate 3 and is then deflected downwards to reach the specimen to be examined on the specimen support 4. As a result of the fact that the X-ray beam S first impinges on the reflector plate 3, the highly energetic component of the radiation us suppressed, that is to say it no longer reaches the actual measuring plane. If an X-ray tube with a molybdenum anode is used, for example, the continuous radiation component of more than 20 KeV penetrates into the reflector plate so that it can no longer reach the specimen support 4. As a result of this elimination of the highly energetic radiation, the X-ray tube can now be operated in the optimum voltage range for the radiation yield. In other words, the stimulating radiation is split into two parts at the reflector 3. The unwanted highly energetic part is eliminated as with a low-pass filter and the low-energy component of the radiation can reach the surface of the specimen support in the optimum manner. Thus a disadvantageous influencing of the background of the specimen supporting plate 4 is eliminated.

Figure 2:
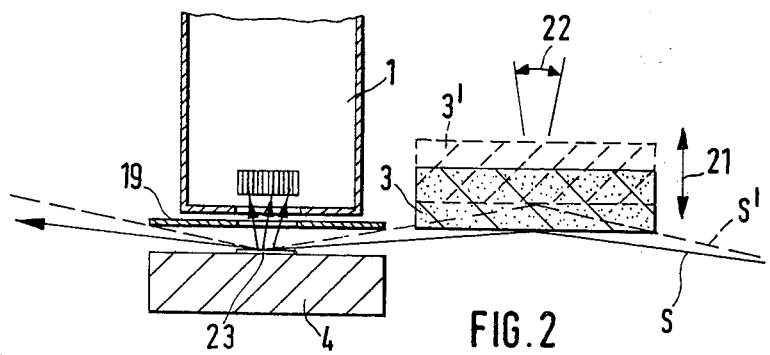
FIG. 2 shows a diagrammatic partial view, in section, of a modified measuring apparatus according to the invention.

The reflector plate 3, which may consist of quartz or another suitable material, for example, is preferably disposed very close to the specimen support 4. The most favorable arrangement is obviously the position illustrated in FIG. 1. If it may be desired for any reason, however, there is also the possibility of a construction as shown in FIG. 2 in which the parts corresponding to FIGS. 1, 3 and 4 are provided with the same reference numerals. In the arrangement shown in FIG. 2, the reflector plate 3 is beside the detector 1 at the height of the aperture diaphragm 19. Here, too, the incident radiation S is deflected at the reflector plate 3 so that only the low-energy component can reach the top of the specimen supporting plate 4. As the arrows 21 and 22 and the reflector 3' shown in broken lines show, the path of the radiation can be altered by adjustment of the height and the angle of the reflector plate 3 so that then, for example, a path of radiation S' results, as indicated in broken lines in FIG. 2. In addition, in FIG. 2, the fluorescence radiation originating from the specimen 23 on the specimen support 4 and entering the detector 1 is also indicated.

With the apparatus according to the invention, apart from the energetic advantages there is also the further advantage that any alignment of the specimen supporting plates to be examined is eliminated. The fine adjustment of the path of rays, which only diverges by an amount of 4 to 6 minutes, for example, in relation to the specimen supporting plate, is effected solely by alignment of the X-ray tube or, with the apparatus shown in FIG. 2, by adjustment of the reflector plate and/or the X-ray tube.

It is, of course, to be understood that the present invention is by no means limited to the specific showing in the drawings but also encompasses any modifications within the scope of the appended claims.

What we claim is:

1. A method of analyzing a specimen with a beam of X-ray radiation by detecting fluorescent radiation emitted by the specimen, the method comprising the steps of:

positioning the sample in alignment with a fluorescent radiation detector and in juxtaposition with a reflector plate having a reflecting surface;

directing a beam of X-ray radiation having high and low energy components toward the reflecting surface at a shallow angle of incidence with respect thereto;

absorbing the high-energy components of the beam in the reflector plate while reflecting the low-energy components of the beam from the reflector plate onto the specimen by selecting an appropriate angle of incidence, and detecting the fluorescent radiation emitted by the specimen due to impingement of the low-energy components on the specimen with the fluorescent radiation detector.

2. The method of claim 1 wherein the reflector plate is made of quartz.

3. The method of claim 2 wherein the angle of incidence is in the range of four to six minutes.

* * * * *